US00PP26637P3

(12) United States Plant Patent
Layt

(10) Patent No.: US PP26,637 P3
(45) Date of Patent: Apr. 19, 2016

(54) ***THEMEDA TRIANDA* PLANT NAMED 'THEM01'**

(50) Latin Name: *Themeda trianda*
Varietal Denomination: THEM01

(71) Applicant: Todd Anthony Layt, Clarendon (AU)

(72) Inventor: Todd Anthony Layt, Clarendon (AU)

( * ) Notice: Subject to any disclaimer, the term of this patent is extended or adjusted under 35 U.S.C. 154(b) by 76 days.

(21) Appl. No.: 14/121,439

(22) Filed: Sep. 5, 2014

(65) Prior Publication Data

US 2016/0073570 P1 Mar. 10, 2016

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Anne Grunberg
(74) *Attorney, Agent, or Firm* — Samuel R. McCoy, Jr.

(57) ABSTRACT

'THEM01' is a distinctive variety of *Themeda trianda* which is characterized by a mounded growth habit, a larger plant size, high shoot density, and a high degree of branching of culms which translates to a compact and dense plant habit.

1 Drawing Sheet

Latin name of the genus and species: The Latin name of the genus and species of the novel variety disclosed herein is *Themeda trianda.*

Variety denomination: The inventive variety of *Themeda trianda* disclosed herein has been given the variety denomination 'THEM01'.

BACKGROUND OF THE INVENTION

The present invention relates to a new and distinct perennial variety of *Themeda trianda*, which has been given the variety denomination of 'THEM01'. Its market class is that of an ornamental grass. 'THEM01' is intended for use as a decorative plant in landscaping and in container gardening.

Parentage: The instant variety of *Themeda trianda* is a seedling selection from openly pollinated *Themeda trianda* 'Mingo' plants, that was finally selected in 2009 at a commercial plant breeding facility in Clarendon, New South Wales Australia. Seed harvested from the parent plant in January 2007 was sown in September of 2007 in accord with standard greenhouse propagation practices. In November of 2008, the resulting young plants were transplanted into 15 cm nursery containers and relocated to an outdoor production area. While inspecting the crop in March of 2008, one plant was observed with a taller plant height and a denser tufting growth habit when compared to the parent. The instant variety was isolated and further observed from March 2008 until January 2009 for confirmation of the stability of the distinguishing characteristics for which it was initially selected. This selection was given the name, 'THEM01'.

Asexual Reproduction: 'THEM01' was first propagated asexually by division in Clarendon, New South Wales Australia in January of 2009 in order to increase the amount of plant germplasm for further evaluation and eventual commercial production, and has since been propagated through three successive generations. The distinctive characteristics of the inventive 'THEM01' variety are stable from generation to generation; clones of the variety produced by asexual reproduction maintain the distinguishing characteristics of the original plant.

SUMMARY OF THE INVENTION

'THEM01' is a distinctive variety of *Themeda trianda* which is characterized by a mounded growth habit, a larger plant size, high shoot density, and a high degree of branching of culms which translates to a compact and dense plant habit.

BRIEF DESCRIPTION OF THE FIGURES

The FIGURE illustrates a mature 'THEM01' plant, at approximately 12 months of age, in a 30 cm pot.

BOTANICAL DESCRIPTION OF THE PLANT

The following is a detailed botanical description of a new and distinct variety of a *Themeda trianda* ornamental grass known as 'THEM01'. Plant observations were made on plants grown in Clarendon, New South Wales, Australia. Unless indicated otherwise, the descriptions disclosed herein are based upon observations made from mature 'THEM01' plants, grown outdoors in full sun, from rooted cuttings from November 2012 to September 2013 in 30 cm nursery pots filled with soilless potting media, fertilized with a single top-dress application of granular slow release fertilizer and regularly watered with automatic overhead irrigation. No pest and disease measures were taken and no plant growth regulators were applied.

Those skilled in the art will appreciate that certain characteristics will vary with older or, conversely, younger plants. 'THEM01' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 1986 edition. Note that generic color descriptions such as 'blue-green' do not exist in the R.H.S. charts and the corresponding R.H.S. colors are quoted.

GROWTH HABIT, DIMENSIONS AND COLOR

Plant description:

*Plant habit*.—Herbaceous perennial; caespitose (i.e. "mounded").

*Height*.—Overall height of 40 to 50 cm at maturity, with most tillers at 30 to 40 cm tall.

*Width*.—Approximately 75 to 90 cm at maturity.

*Bloom period*.—Summer.

*Hardiness*.—USDA Zone 9 to 11.

*Environmental tolerances*.—Drought tolerance in common with the species. Prefers full to filtered sun and regular watering but can tolerate periods of drought once established. Low salinity tolerance. Low to moderate frost tolerance.

*Pest and disease susceptibility or resistance*.—In common with the species, none of note.

*Propagation*.—Propagation is accomplished by vegetative propagation. In vegetative propagation, large and mature stock plants are manually divided into large clumps, taking great care not to disturb the roots; these clumps are transplanted into appropriately sized nursery container or propagation trays. These containers are filled with an appropriate potting media of a free draining and soilless substrate designed for an optimal combination of air porosity, moisture and nutrients yet also freely drains when saturated with rain or irrigation water, often referred to as a propagation mix. Once transplanted, these newly planted divisions will begin to root in approximately 4 weeks but could take many months and up to a year to fully rebound. In commercial production, an average crop time is approximately 4 to 6 months to produce a mature and marketable 15 cm nursery container, starting from a rooted cutting.

Roots: Dense, fibrous root system.

Stem:

*Branching and habit*.—Tufts of highly branched culms that terminate with fans of long slender foliage.

*Number of culms*.—Numerous; observed as more than 30 per 15 mm pot and tightly oriented in the center of the pot.

*Culm attitude*.—Branching attitude is upright and outward but culms tend to weep from the weight of the foliage.

*Culm dimensions*.—Ranging from 20 to 35 cm with a diameter ranging from 21.0 to 2.5 mm.

*Culm internodes*.—Ranging from 13 to 22 mm, as measured.

*Stem strength*.—Strong.

*Shape*.—Cylindrical and somewhat flattened.

*Culm color*.—Mature, woody culms are closest to greyed-yellow 161C.

*Stem surface*.—Smooth; glabrous.

Lamina:

*Type*.—Evergreen in tropical climate.

*Arrangement*.—Alternate.

*Attachment*.—Cauline.

*Division*.—Simple.

*Shape*.—Linear.

*Shape; apex*.—Acute.

*Leaf aspect*.—Predominantly flat.

*Venation*.—Parallel.

*Vein color* (*adaxial and abaxial surfaces*).—Indistinguishable from surrounding foliage.

*Margins*.—Entire.

*Surfaces* (*adaxial & abaxial surface*).—Glabrous.

*Mature leaf dimensions*.—Between 4 to mm in length, and approximately 200 to 325 mm.

*Leaf color* (*adaxial & abaxial surfaces*).—Juvenile & mature: a combination of green 135D to 136D to 128C, depending on amount of glaucosity which varies throughout. Predominant color is green 128C. 137B. In summer, hues of purple 77C appear, randomly, throughout the foliage.

*Leaf sheath*.—Glabrous, ranging from 20 to 30 mm long. Color is a combination of Green 130D, Red-purple 62D, and Red-purple 63C. Apex is acute.

*Collar*.—Indistinguishable.

*Ligule*.—Short; apex rounded; sparse hairs.

*Auricle*.—Absent.

Inflorescence: Not yet observed.

Spikelets: Not yet described.

Fruit and seed production: Not yet described.

Comparison of THEM01 with other varieties of *Themeda trianda: Themeda* sp. is an under-commercialized Genus of ornamental grass. Consequently, there has been little breeding done to select for improved characteristics such as those claimed with regard to 'THEM01'. Accordingly, comparisons will be made between 'THEM01' and the parent, *Themeda trianda* 'Mingo', which is the only improved variety known to the breeder that exhibits a similar growth habit. By comparison to the parent, 'THEM01' is a larger plant with a mounded habit and exhibits a higher degree of shoot density and branching of culms. At maturity, the plant size dimensions of 'THEM01' are 40 to 50 cm tall and 75 to 90 cm wide whereas the dimensions of 'Mingo' are 20 to 25 cm tall and 60 cm wide. The difference in overall dimensions is due in large part to a difference in growth habits. 'Mingo' has a prostrate growth habit whereas the habit of 'THEM01' is considered mounded. A contributing factor in the mounding habit of 'THEM01' is the strong, woody nature of the culms compared to the weaker, herbaceous culms of 'Mingo'. 'THEM01' also appears to have a denser growth habit. The increased density is due to the high degree of culm branching, compared to the less branched 'Mingo'. 'THEM01' also has a greater number of shoots or "tillers" per pot. As observed, 'THEM01' has approximately 30 shoots per 15 cm nursery pot whereas 'Mingo' plants of the same age have approximately 20 shoots per pot.

That which is claimed is:

1. A new and distinct variety of *Themeda trianda* plant named 'THEM01', substantially as described and illustrated herein.

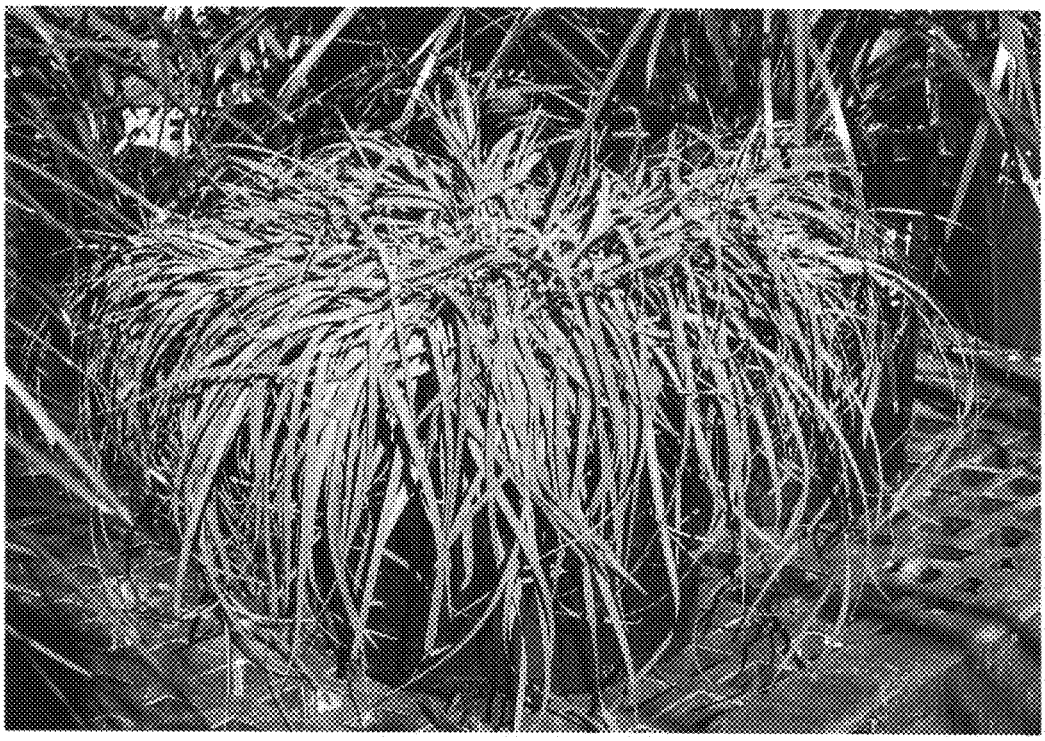

* * * * *